United States Patent
Chakraborty et al.

(10) Patent No.: US 10,405,866 B2
(45) Date of Patent: Sep. 10, 2019

(54) LEFT ATRIAL APPENDAGE OCCLUSION DEVICE

(71) Applicant: Flow MedTech, Inc, Dallas, TX (US)

(72) Inventors: Arnab Ranjan Chakraborty, Johnson City, TN (US); Christine Tu-Anh Hang, Aiken, SC (US)

(73) Assignee: FLOW MEDTECH, INC, Dallas, TX (US)

( * ) Notice: Subject to any disclaimer, the term of this patent is extended or adjusted under 35 U.S.C. 154(b) by 150 days.

(21) Appl. No.: 15/306,611

(22) PCT Filed: Apr. 24, 2015

(86) PCT No.: PCT/US2015/027666
§ 371 (c)(1),
(2) Date: Oct. 25, 2016

(87) PCT Pub. No.: WO2015/164836
PCT Pub. Date: Oct. 29, 2015

(65) Prior Publication Data
US 2017/0042550 A1    Feb. 16, 2017

Related U.S. Application Data

(60) Provisional application No. 61/984,342, filed on Apr. 25, 2014.

(51) Int. Cl.
*A61B 17/12*    (2006.01)

(52) U.S. Cl.
CPC .. *A61B 17/12122* (2013.01); *A61B 17/12031* (2013.01); *A61B 17/12136* (2013.01); *A61B 2017/1205* (2013.01)

(58) Field of Classification Search
CPC ........ A61B 17/12031; A61B 17/12136; A61B 17/12122; A61B 2017/1205
See application file for complete search history.

(56) References Cited

U.S. PATENT DOCUMENTS

| 4,836,204 A | * | 6/1989 | Landymore ........ A61B 17/0057 |
| | | | 604/101.05 |
| 4,917,089 A | | 4/1990 | Sideris |
| 5,433,727 A | | 7/1995 | Sideris |

(Continued)

FOREIGN PATENT DOCUMENTS

| WO | WO2007130724 A2 | 11/2007 |
| WO | 2013068466 A1 | 5/2013 |
| WO | 2013192332 A2 | 12/2013 |

OTHER PUBLICATIONS

European Search Report and Written Opinion dated Nov. 16, 2017 for European Patent Application No. 15783150.4.

(Continued)

*Primary Examiner* — Phong Son H Dang
(74) *Attorney, Agent, or Firm* — Morris, Manning & Martin, LLP; Bryan D. Stewart

(57) ABSTRACT

An exemplary occlusion device is disclosed. In various embodiments, the exemplary occlusion device includes a cap chamber and a bulb chamber for occluding a left atrial appendage (LAA). In particular embodiments, after delivery to the LAA, the cap chamber and the bulb chamber are each inflated via various amounts of fluid(s) to occlude the LAA.

16 Claims, 12 Drawing Sheets

(56) References Cited

U.S. PATENT DOCUMENTS

| | | | |
|---|---|---|---|
| 5,634,936 A * | 6/1997 | Linden | A61B 17/0057 604/60 |
| 5,792,179 A | 8/1998 | Sideris | |
| 6,019,778 A | 2/2000 | Wilson et al. | |
| 6,123,715 A | 9/2000 | Amplatz | |
| 6,152,144 A | 11/2000 | Lesh et al. | |
| 6,238,416 B1 | 5/2001 | Sideris | |
| 6,293,960 B1 * | 9/2001 | Ken | A61B 17/12113 606/195 |
| 6,368,339 B1 | 4/2002 | Amplatz | |
| 6,375,668 B1 * | 4/2002 | Gifford | A61B 17/12022 606/200 |
| 6,447,531 B1 | 9/2002 | Amplatz | |
| 6,579,303 B2 | 6/2003 | Amplatz | |
| 6,652,556 B1 * | 11/2003 | VanTassel | A61B 17/12122 606/200 |
| 6,730,108 B2 | 5/2004 | Van Tassel et al. | |
| 6,949,113 B2 * | 9/2005 | Van Tassel | A61B 17/0057 606/200 |
| 6,981,980 B2 * | 1/2006 | Sampson | A61F 5/003 606/192 |
| 6,994,092 B2 | 2/2006 | Van Der Burg et al. | |
| 7,128,073 B1 | 10/2006 | Van Der Burg et al. | |
| 7,152,605 B2 | 12/2006 | Khairkhahan et al. | |
| 7,284,488 B2 | 10/2007 | Maruyama et al. | |
| 7,318,829 B2 | 1/2008 | Kaplan et al. | |
| 7,537,012 B2 | 5/2009 | Mohanraj | |
| 7,566,336 B2 | 7/2009 | Corcoran et al. | |
| 7,597,704 B2 | 10/2009 | Frazier et al. | |
| 7,665,466 B2 | 2/2010 | Figulla et al. | |
| 7,842,069 B2 * | 11/2010 | Widomski | A61B 17/0057 606/213 |
| 7,955,354 B2 | 6/2011 | Figulla et al. | |
| 8,080,032 B2 | 12/2011 | Van Der Burg et al. | |
| 8,097,015 B2 * | 1/2012 | Devellian | A61B 17/0057 606/200 |
| 8,100,938 B2 | 1/2012 | Figulla et al. | |
| 8,152,758 B2 | 4/2012 | Chan et al. | |
| 8,221,445 B2 | 7/2012 | Van Tassel et al. | |
| 8,523,897 B2 | 9/2013 | Van Der Burg et al. | |
| 8,535,343 B2 | 9/2013 | Van Der Burg et al. | |
| 8,545,530 B2 * | 10/2013 | Eskridge | A61B 17/12022 606/191 |
| 8,562,643 B2 | 10/2013 | Tekulve et al. | |
| 8,597,324 B2 | 12/2013 | Briganti et al. | |
| 8,636,732 B2 | 1/2014 | Davis et al. | |
| 8,636,764 B2 | 1/2014 | Miles et al. | |
| 8,647,361 B2 | 2/2014 | Borillo et al. | |
| 8,663,245 B2 | 3/2014 | Francischelli et al. | |
| 8,663,268 B2 | 3/2014 | Quinn et al. | |
| 8,663,273 B2 | 3/2014 | Khairkhahan et al. | |
| 8,685,055 B2 | 4/2014 | Vantassel et al. | |
| 8,690,910 B2 | 4/2014 | Carley et al. | |
| 8,690,911 B2 | 4/2014 | Miles et al. | |
| 8,715,302 B2 | 5/2014 | Ibrahim et al. | |
| 8,715,318 B2 | 5/2014 | Miles et al. | |
| 8,721,663 B2 | 5/2014 | Kaplan et al. | |
| 8,740,934 B2 | 6/2014 | McGuckin, Jr. | |
| 8,747,452 B2 | 6/2014 | Fischell et al. | |
| 8,747,454 B2 | 6/2014 | Khairkhahan et al. | |
| 8,753,303 B2 | 6/2014 | Weisman et al. | |
| 8,764,765 B2 | 7/2014 | Piskun et al. | |
| 8,764,793 B2 | 7/2014 | Lee | |
| 8,814,931 B2 | 8/2014 | Wang et al. | |
| 9,770,234 B2 * | 9/2017 | Sideris | A61B 17/0057 |
| 10,076,335 B2 * | 9/2018 | Zaver | A61B 17/0057 |
| 2003/0114913 A1 * | 6/2003 | Spenser | A61F 2/2412 623/1.11 |
| 2003/0149463 A1 | 8/2003 | Solymar | A61B 17/0057 623/1.1 |
| 2004/0254594 A1 * | 12/2004 | Alfaro | A61B 17/0057 606/151 |
| 2005/0004652 A1 | 1/2005 | Van Der Burg et al. | |
| 2005/0033331 A1 * | 2/2005 | Burnett | A61B 5/14539 606/154 |
| 2005/0070957 A1 | 3/2005 | Das | |
| 2005/0113861 A1 | 5/2005 | Corcoran et al. | |
| 2005/0177182 A1 | 8/2005 | Van Der Burg et al. | |
| 2005/0216052 A1 | 9/2005 | Mazzocchi et al. | |
| 2005/0234543 A1 | 10/2005 | Glaser et al. | |
| 2006/0020278 A1 * | 1/2006 | Burnett | A61B 5/14539 606/153 |
| 2006/0020327 A1 * | 1/2006 | Lashinski | A61F 2/2436 623/1.25 |
| 2006/0265043 A1 | 11/2006 | Mandrusov et al. | |
| 2007/0083224 A1 * | 4/2007 | Hively | A61F 5/0036 606/192 |
| 2007/0083230 A1 | 4/2007 | Javois | |
| 2007/0129753 A1 | 6/2007 | Quinn et al. | |
| 2007/0135826 A1 | 6/2007 | Zaver et al. | |
| 2007/0179345 A1 | 8/2007 | Santilli | |
| 2008/0033457 A1 | 2/2008 | Francischelli et al. | |
| 2009/0099596 A1 | 4/2009 | McGuckin, Jr. et al. | |
| 2009/0149879 A1 * | 6/2009 | Dillon | A61F 5/0033 606/192 |
| 2009/0171428 A1 | 7/2009 | Hansen | |
| 2009/0209999 A1 * | 8/2009 | Afremov | A61B 17/0057 606/213 |
| 2010/0185233 A1 * | 7/2010 | Thommen | A61B 17/0057 606/213 |
| 2011/0022079 A1 | 1/2011 | Miles et al. | |
| 2011/0178539 A1 | 7/2011 | Holmes, Jr. et al. | |
| 2011/0288558 A1 | 11/2011 | Nimgaard | |
| 2012/0116269 A1 | 5/2012 | McAuley | |
| 2012/0191125 A1 * | 7/2012 | Babkes | A61F 5/0033 606/192 |
| 2012/0271343 A1 | 10/2012 | Borillo et al. | |
| 2012/0283585 A1 | 11/2012 | Werneth et al. | |
| 2012/0283773 A1 | 11/2012 | Van Tassel et al. | |
| 2012/0289776 A1 * | 11/2012 | Keast | A61B 17/221 600/106 |
| 2013/0018413 A1 * | 1/2013 | Oral | A61B 5/0031 606/213 |
| 2013/0116724 A1 | 5/2013 | Clark et al. | |
| 2013/0138138 A1 | 5/2013 | Clark et al. | |
| 2013/0190799 A1 | 7/2013 | Clark | |
| 2013/0218192 A1 | 8/2013 | Erzberger et al. | |
| 2013/0218193 A1 | 8/2013 | Erzberger et al. | |
| 2013/0237908 A1 | 9/2013 | Clark | |
| 2013/0331884 A1 | 12/2013 | Van Der Burg et al. | |
| 2013/0338696 A1 | 12/2013 | Sideris | |
| 2014/0039536 A1 | 2/2014 | Cully et al. | |
| 2014/0058371 A1 | 2/2014 | Krishnan | |
| 2014/0074151 A1 | 3/2014 | Tischler et al. | |
| 2014/0100596 A1 | 4/2014 | Rudman et al. | |
| 2014/0107696 A1 | 4/2014 | Borillo et al. | |
| 2014/0114340 A1 | 4/2014 | Zhou et al. | |
| 2014/0163605 A1 | 6/2014 | Van Tassel et al. | |
| 2014/0188157 A1 | 7/2014 | Clark | |
| 2015/0151826 A1 * | 6/2015 | Geneste | B64B 1/58 244/31 |
| 2016/0100843 A1 | 4/2016 | Sideris | |
| 2016/0192912 A1 * | 7/2016 | Kassab | A61B 17/0057 606/200 |
| 2017/0143318 A1 * | 5/2017 | Hu | A61B 17/0057 |
| 2018/0338767 A1 * | 11/2018 | Dasnurkar | A61B 17/12168 |
| 2018/0360432 A1 | 12/2018 | Corcoran et al. | |
| 2018/0368820 A1 | 12/2018 | Rad et al. | |
| 2018/0368855 A1 | 12/2018 | Edmiston et al. | |
| 2018/0368856 A1 | 12/2018 | Miles et al. | |
| 2018/0369594 A1 | 12/2018 | Werneth et al. | |
| 2019/0000604 A1 | 1/2019 | Eli | |
| 2019/0008495 A1 | 1/2019 | Li | |
| 2019/0008626 A1 | 1/2019 | Janardhan et al. | |
| 2019/0009057 A1 | 1/2019 | Li et al. | |
| 2019/0015109 A1 | 1/2019 | Li | |
| 2019/0021711 A1 | 1/2019 | Li | |
| 2019/0021741 A1 | 1/2019 | Chen et al. | |
| 2019/0038294 A1 | 2/2019 | Tieu et al. | |
| 2019/0038316 A1 | 2/2019 | Gillespie et al. | |
| 2019/0046170 A1 | 2/2019 | Coyle et al. | |

(56) References Cited

U.S. PATENT DOCUMENTS

| | | |
|---|---|---|
| 2019/0046210 A1 | 2/2019 | Bowman |
| 2019/0046213 A1 | 2/2019 | Gong et al. |
| 2019/0053810 A1 | 2/2019 | Griffin |
| 2019/0069901 A1 | 3/2019 | Forbes |
| 2019/0071800 A1 | 3/2019 | Koppe |
| 2019/0076136 A1 | 3/2019 | Zhang |
| 2019/0083075 A1 | 3/2019 | Onushko et al. |
| 2019/0088368 A1 | 3/2019 | Grodzki et al. |
| 2019/0090841 A1 | 3/2019 | Degertekin et al. |
| 2019/0090884 A1 | 3/2019 | Bowman |
| 2019/0090885 A1 | 3/2019 | Zhou et al. |
| 2019/0090945 A1 | 3/2019 | Whayne et al. |
| 2019/0090951 A1 | 3/2019 | Camus et al. |
| 2019/0099062 A1 | 4/2019 | Ishihara et al. |
| 2019/0110796 A1 | 4/2019 | Jayaraman |
| 2019/0110880 A1 | 4/2019 | Fox et al. |
| 2019/0117204 A1 | 4/2019 | Wang et al. |
| 2019/0117229 A1 | 4/2019 | Ibrahim et al. |
| 2019/0117260 A1 | 4/2019 | Ahmad |
| 2019/0117300 A1 | 4/2019 | Whayne et al. |
| 2019/0125302 A1 | 5/2019 | Clark |
| 2019/0125350 A1 | 5/2019 | Fung et al. |
| 2019/0125362 A1 | 5/2019 | Tischler |
| 2019/0125375 A1 | 5/2019 | Palushi et al. |
| 2019/0125400 A1 | 5/2019 | Ibrahim et al. |
| 2019/0125439 A1 | 5/2019 | Rohl et al. |
| 2019/0125513 A1 | 5/2019 | Purcell et al. |
| 2019/0125938 A1 | 5/2019 | Chen et al. |

OTHER PUBLICATIONS

International Search Report and Written Opinion for related International Patent Application PCT/US2015/027666 dated Jul. 28, 2015.
"Transcatheter Patch." Custom Medical Devices. Custom Medical Devices, n.d. Web. Jul. 29, 2014. http://www.custommedicaldevices.net/products/transcatheter-patch/.
European Search Report and Written Opinion dated Sep. 3, 2018 for European Patent Application No. 15842602.3.
International Search Report and Written Opinion dated Dec. 17, 2015 for International Patent Application No. PCT/US2015/05967.

* cited by examiner

LEFT ATRIAL APPENDAGE OCCLUSION DEVICE

CROSS REFERENCE TO RELATED APPLICATIONS

This application claims the benefit of and priority under 35 U.S.C. § 371 to International Patent Application No. PCT/US2015/027666, filed Apr. 24, 2015, entitled "Left Atrial Appendage Occlusion Device," which claims priority to U.S. Provisional Patent Application No. 61/984,342, filed Apr. 25, 2014, entitled, "Left Atrial Appendage Occlusion Device" each of which are incorporated herein by reference in their entireties.

TECHNICAL FIELD

The present disclosure relates generally to medical devices.

BACKGROUND

The left atrial appendage (LAA) originates from the left wall of the left atrium. This fingerlike projection opens to the atrium through an ovoid orifice and extends 2-4 cm long, pointing towards the apex.

Atrial fibrillation (AF) is the most common arrhythmia (i.e. irregularly timed contraction) and oftentimes occurs due to sustained increased left atrial afterload—leading to an enlargement of the left atrium (LA). The presence of AF may establish a positive feedback loop that furthers enlargement and increases the probability of thrombus (i.e. clotting) formation. As the LAA is not contracting on time, blood stasis occurs in the appendage as the blood flows into the appendage but does not flow out in a rhythmic fashion. This leads to blood clotting in the appendage, which then becomes a risk as the irregular contraction of the LAA may force the clot to travel out of the appendage and into the brain, leading to an ischemic stroke.

It is believed by researchers that up to 90 percent of the clots found in the brain come from the LAA. If AF patients are not treated, their risk of stroke increases as they age; 15 percent of all strokes are caused by AF. However, in patients 70 years and older, more than 20 to 25 percent of strokes are caused by atrial fibrillation.

Current research suggests that occlusion of the left atrial appendage reduces the risk of ischemic stroke in atrial fibrillation patients by preventing LAA thrombus formation from occurring. It also acts as an alternative therapy to oral anticoagulation (OAC). Some patients elect to not take OACs or are ineligible due to side effects.

BRIEF SUMMARY OF THE DISCLOSURE

According to particular embodiments, the present disclosure includes an occlusion device for occluding a left atrial appendage, the device including: A) a connection system configured for attaching an occlusion device to a fluid transport device; and B) an inflatable balloon operatively fastened to the connection system, the inflatable balloon including a cap chamber and a bulb chamber, the cap chamber and the bulb chamber separated by an elastomeric wall, wherein: 1) the connection system a) extends through the cap chamber and at least partially through the bulb chamber, b) is configured for delivering one or more fluids to the cap chamber and the bulb chamber, and c) includes one or more values; 2) the cap chamber is substantially disc-shaped and is configured to expand outwardly in a lateral direction from a center of the cap chamber to substantially fill a first portion of a left atrial appendage; and 3) the bulb chamber is configured to expand outwardly to substantially fill a second portion of the left atrial appendage.

In various embodiments, a device, the device including: A) a connection system configured for attaching the device to a fluid transport device, the connection system extending at least partially through each of a cap chamber and a bulb chamber of an inflatable balloon and is configured for delivering one or more fluids to the cap chamber and the bulb chamber; and B) the inflatable balloon, wherein the inflatable balloon is operatively connected to the connection system and includes: 1) the cap chamber, wherein the cap chamber is configured to expand outwardly in a lateral direction from a center of the cap chamber; and 2) the bulb chamber, wherein the bulb chamber is separated from the cap chamber by an elastomeric wall and is configured to expand outwardly to substantially fill a void.

In one or more embodiments, a method for occluding a left atrial appendage, the method including providing an occlusion device including a connection system operatively connected to a balloon system, wherein: A) the connection system fluidly connects a first chamber and second chamber of the balloon system via at least one valve; B) the balloon system is configured to be: 1) passed through a catheter system; 2) at least partially inflated such that a first chamber of the balloon system expands in a lateral direction for substantially filling a first portion of a left atrial appendage of a patient; and 3) inflated such that a second chamber of the balloon system expands for substantially filling a second portion of the left atrial appendage of the patient.

BRIEF DESCRIPTION OF THE DRAWINGS

Further features and benefits of the present disclosure will be apparent from a detailed description of various embodiments thereof taken in conjunction with the following drawings, wherein similar elements are referred to with similar reference numbers, and wherein.

DETAILED DESCRIPTION

Figure 1:
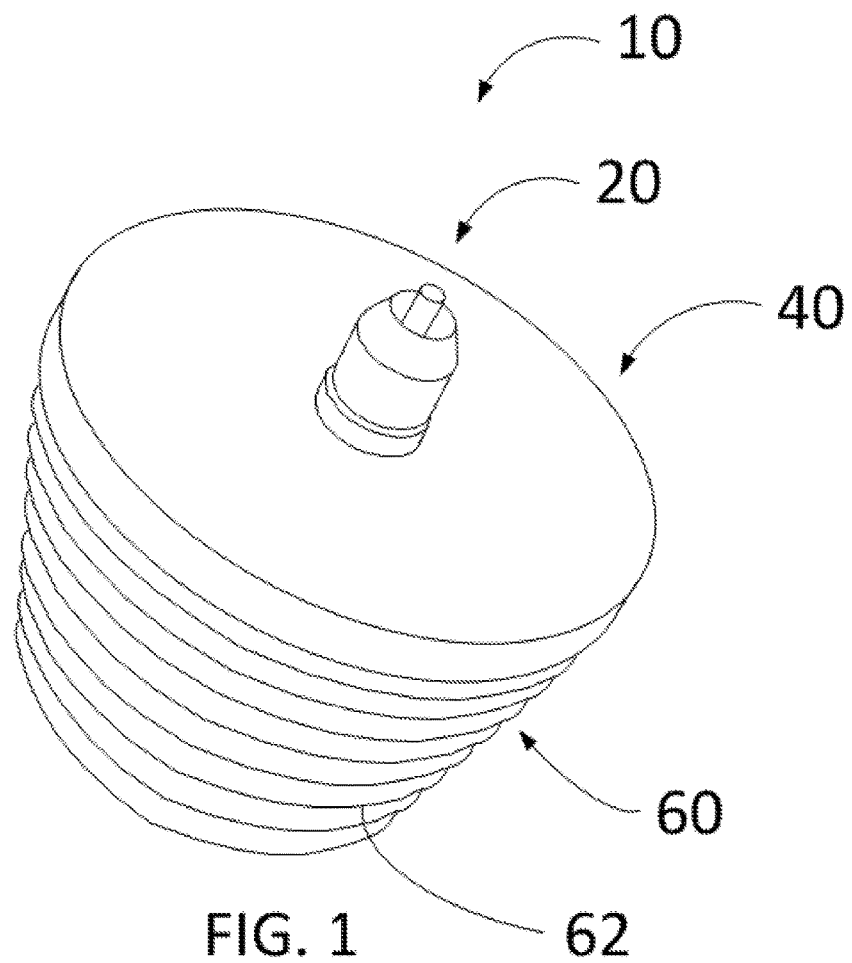
FIG. 1 is a side view of an exemplary occlusion device in a substantially uninflated state, according to one embodiment of the present disclosure.

Whether or not a term is capitalized is not considered definitive or limiting of the meaning of a term. As used in this document, a capitalized term shall have the same meaning as an uncapitalized term, unless the context of the usage specifically indicates that a more restrictive meaning for the capitalized term is intended. However, the capitalization or lack thereof within the remainder of this document is not intended to be necessarily limiting unless the context clearly indicates that such limitation is intended.

For the purpose of promoting an understanding of the principles of the present disclosure, reference will now be made to the embodiments illustrated in the figures and specific language will be used to describe the same. It will, nevertheless, be understood that no limitation of the scope of the disclosure is thereby intended; any alterations and further modifications of the described or illustrated embodiments, and any further applications of the principles of the disclosure as illustrated therein are contemplated as would normally occur to one skilled in the art to which the disclosure relates. All limitations of scope should be determined in accordance with and as expressed in the claims.

Overview

The present disclosure relates generally, according to particular embodiments, to an implantable, inflatable device including soft polymeric material(s), one-way sealing system, multiple layers, and insertable fluid for inflation. In various embodiments, the present disclosure relates to an implantable, inflatable device for soft tissue closures such as left atrial appendages.

Various embodiments of the device disclosed herein may be customizable with a high number of usability cases, have a low risk of perforation, have a low risk of bleeding, be deployed through typical transseptal procedure, be used in lieu of anticoagulants or for patients who cannot take anticoagulants, promote immediate occlusion, and not heavily rely on endothelialization.

An exemplary occlusion device includes a connection system, cap chamber, and a bulb chamber. In particular embodiments, the connection system consists of a secure attachment method for interaction between the device and delivery system. In various embodiments, fluid transport and passage channels lie within the connection system to facilitate fluid delivery. In some embodiments, valves are also featured within the connection system to control fluid flow and to separate the multiple chambers of the device. As further discussed below, in at least one embodiment, the cap chamber consists of fluid passage channels and a fluid ring to allow for the cap chamber to expand laterally from the fluid transport channel.

In particular embodiments, the bulb chamber and cap chamber are manufactured out of soft polymeric material(s) and are separated by an elastomeric wall and valve(s). In various embodiments, a bulb chamber consists of a textured surface, interior chamber, and second interior chamber. The textured surface of the bulb chamber may provide a manner to interact with the LAA, and the interior chamber(s) may allow for a method of inflating the bulb chamber to provide anchoring and stability within the LAA.

The present disclosure depicts an exemplary device as used within a left atrial appendage within a patient's heart, although it will be understood by one of ordinary skill in the art that exemplary device embodiments discussed herein may be used in a variety of ways and should not be limited to uses within a patient's heart. In a particular embodiment, an exemplary device may be used to occlude the LAA to help prevent a stroke in the patient. In this particular embodiment, a closure procedure may be done under standard transcatheterization and transseptal techniques using transesophageal echocardiogram (TEE) and contrast fluoroscopy (fluoro). Continuing with this particular embodiment, after the delivery system is directed to the LAA, the occlusion device is deployed. The device, in this particular embodiment, contains various inflation states ranging from partial to full inflation based on the amount of fluid inserted into the device using the fluid delivery system. As will be understood by one of ordinary skill in the art, in this particular embodiment, once all chambers are inflated to adapt to the surrounding LAA anatomy and provide occlusion to prevent blood flow from entering the LAA, full inflation has been reached. Continuing with this particular embodiment, the device is detached from the delivery system and remains in the LAA and the delivery system is removed from the body.

Exemplary Device Structure

Turning now to the figures, in the embodiment shown in FIG. 1, an exemplary occlusion device 10 includes: 1) a connection system 20; and 2) an inflatable balloon including a cap chamber 40 and a bulb chamber 60. In various embodiments, the connection system 20 is operatively connected to the cap chamber 40 and the bulb chamber 60 by a suitable fastener, such as, for example, an adhesive (e.g., fibrin glue, tissue sealants, hydrogels, tissue glues, etc.). In one or more embodiments, the connection system 20 is operatively connected to the cap chamber 40 and the bulb chamber 60 by a helical thread, which may be constructed of metal material(s) (e.g., aluminum, nitinol, stainless steel, etc.), a twist lock method, which may be constructed of metal material(s) (e.g., aluminum, nitinol, stainless steel, etc.) or polymeric material(s), or a luer lock method, which may be constructed of metal material(s) (e.g., aluminum, nitinol, stainless steel, etc.)or polymeric material(s).

Figure 2:
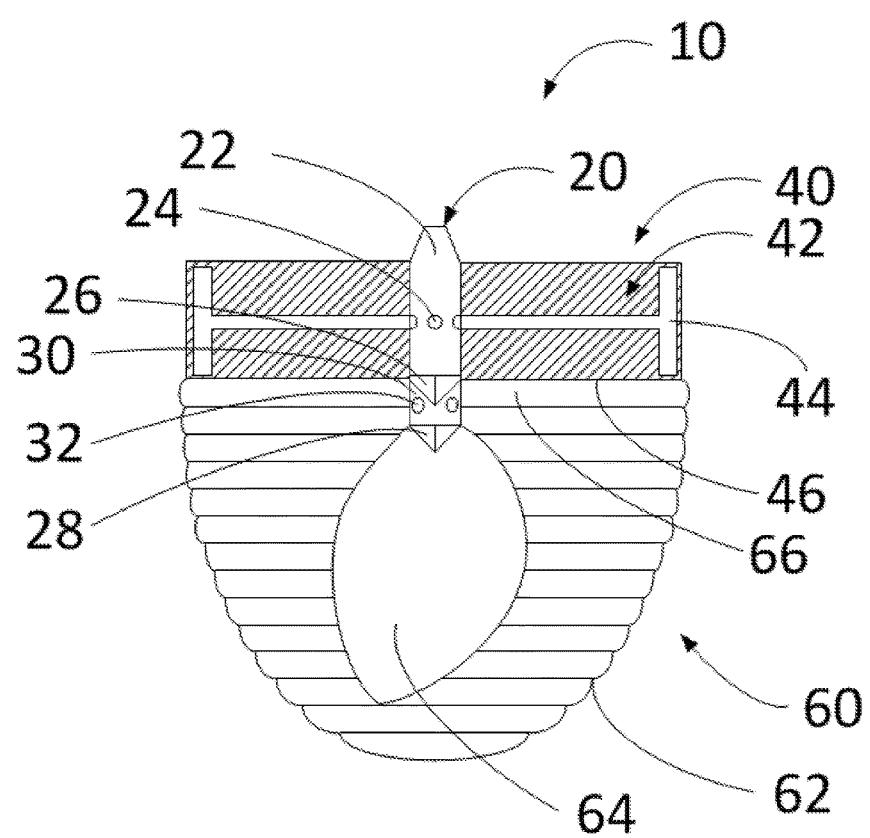
FIG. 2 is a partial cross-sectional view of the exemplary occlusion device in the substantially uninflated state of FIG. 1, according to one embodiment of the present disclosure.

Turning now to FIG. 2, a partial cross-section of the exemplary occlusion device of FIG. 1 is shown. In the embodiment shown in FIG. 2, the connection system 20 includes a fluid passage body 22, one or more fluid passage channels 24, a first valve 26, a second valve 28, inner fluid passage channel 30, and an inner fluid passage opening 32. As will be understood by one of ordinary skill in the art, connection system 20 allows an exemplary occlusion device 10, in embodiments that include a helical thread or twist lock (and other embodiments), to securely attach to a device delivery system. As will be further discussed herein, in various embodiments, fluid is inserted into the exemplary occlusion device 10 through connection system 20 and dispersed through one or more fluid passages through a fluid ring 44 in order to expand a cap chamber 40.

In particular embodiments, the fluid passage body 22, which may be constructed of polymeric material(s) (e.g., polyurethane, silicone, latex, polyurethanes, silicones, latex, nylons, Pebax, PET, PE and other polyolefines, PVC, etc.), is in a particular embodiment, fastened by a welding technique to the connection system 20 and the cap chamber 40. In one embodiment, the fluid passage body 22 is a body that facilitates the transport of fluid to the fluid ring 44 and into the bulb chamber 60.

In various embodiments, the fluid passage channel 24 is made from polymeric material(s) (e.g., polyurethane, silicone, latex, polyurethanes, silicones, latex, nylons, Pebax, PET, PE and other polyolefines, PVC, etc.) and is found within the cap body 42. In at least one embodiment, the fluid passage channel 24 is attached to fluid passage body 22 by a welding technique. In various embodiments, the fluid passage channel 24 contains one or more channels, which can be straight cylindrical shape, curved cylindrical shape, etc., to deliver fluid to the fluid ring 44.

In some embodiments, the valve 26, which may be constructed of polymeric material(s) (e.g., polyurethane, silicone, latex, polyurethanes, silicones, latex, nylons, Pebax, PET, PE and other polyolefines, PVC, etc.), is found fastened through methods such as, but not limited to, adhesives, molding, welding, and etc. to the elastomeric wall 46 and the inner fluid passage channel 30 at the proximal end of fluid passage body 22 and is configured to control fluid insertion into bulb chamber 60. In various embodiments, the valve 26 is a one-way valve. In one or more embodiments, the valve 26 is a check valve. In some embodiments, the valve 26 is any other suitable type of valve, such as, for example, duckbill valve, umbrella valve, or Belleville valve.

According to particular embodiments, the valve 28, which may be made from polymeric material(s) (e.g., polyurethane, silicone, latex, polyurethanes, silicones, latex, nylons, Pebax, PET, PE and other polyolefines, PVC, etc.), is fastened to the inner fluid passage channel 30 and the interior chamber 64 through methods such as, but not limited to, adhesives, molding, welding, and etc. and is configured to control the transport of fluid into interior chamber 64. In various embodiments, the valve 28 is a one-way valve. In one or more embodiments, the valve 28 is a check valve. In some embodiments, the valve 28 is any other suitable type of valve, such as, for example, duckbill valve, umbrella valve, and Belleville valve.

The inner fluid passage channel 30, which may be made of polymeric material(s) (e.g., polyurethane, silicone, latex, polyurethanes, silicones, latex, nylons, Pebax, PET, PE and other polyolefines, PVC, etc.), is, in some embodiments, fastened between the elastomeric wall 46 and the interior chamber 64 through methods such as, but not limited to, adhesives, molding, welding, and etc. and allows controlled fluid transport between the valve 26 and the valve 28 and into second inner chamber 66 through the inner fluid passage opening 32.

In one embodiment, the inner fluid passage opening 32 may include one or more openings that allow fluid transport into the second inner chamber 66. In some embodiments, these openings may be in elliptical, ovular, circular, slot, etc. shapes.

Continuing with FIG. 2, in the embodiment shown, the inflatable balloon includes the cap chamber 40. The cap chamber 40, in the embodiment shown in FIG. 2, includes the cap body 42, the fluid ring 44, and the elastomeric wall 46. In particular embodiments, the cap chamber 40 laterally expands through the inflation of fluid ring 44 to provide occlusion at a first portion of a left atrial appendage.

In various embodiments, the cap body 42, which may be made of polymeric material(s) (e.g., polyurethane, silicone, latex, polyurethanes, silicones, latex, nylons, Pebax, PET, PE and other polyolefines, PVC, etc.), is the main source of support for the cap chamber 40 and is found surrounding fluid ring 44 and proximal to the elastomeric wall 46.

In various embodiments, the fluid ring 44, which may be made of polymeric material(s) (e.g., polyurethane, silicone, latex, polyurethanes, silicones, latex, nylons, Pebax, PET, PE and other polyolefines, PVC, etc.), will inflate through an increased presence of fluid facilitated by transport from the one or more fluid passage channels 24 throughout the cap body 42 to enable the lateral expansion of the cap chamber 40.

In particular embodiments, the elastomeric wall 46 is a barrier, which may be made of polymeric material(s) (e.g., polyurethane, silicone, latex, polyurethanes, silicones, latex, nylons, Pebax, PET, PE and other polyolefines, PVC, etc.), to separate the distal cap chamber 40 from the proximal bulb chamber 60. In particular embodiments, the elastomeric wall 46 provides support and rigidity as there is an increase of lateral expansion of the cap chamber 40.

In various embodiments, the elastomeric wall 46 is constructed concurrently and an integral part with the cap chamber 40 and bulb chamber 60 through molding techniques. In some embodiments, the wall may be constructed by welding techniques or adhesives with either the cap chamber 40 or bulb chamber 60.

In the embodiment shown in FIG. 2, the inflatable balloon further includes the bulb chamber 60. The bulb chamber 60, in particular embodiments, includes an outer textured surface 62, an interior chamber 64, and a second interior chamber 66. The bulb chamber 60 will be inflated in order to reinforce occlusion of a left atrial appendage (LAA) and provide anchoring and stability of the embodiment shown in FIG. 2 inside a LAA.

According to at least one embodiment, the outer textured surface 62, which may be constructed of polymeric material(s) (e.g., polyurethane, silicone, latex, polyurethanes, silicones, latex, nylons, Pebax, PET, PE and other polyolefines, PVC, etc.), is found on the exterior of the bulb chamber 60 and can provide interaction between the bulb chamber 60 and a left atrial appendage. In one embodiment, an outer textured surface 62 can be shaped as ridges. In some embodiments, an outer textured surface 62 is an integral part of the bulb chamber 60 and can be patterned or protruding outwards from the bulb chamber 60, at various angles. In various embodiments, outer textured surface 62 is applied on the bulb chamber 60 through a microfabrication technique. In some embodiments, an outer textured surface 62 with angles can be formed through molding techniques or by coating with unvulcanized or partially vulcanized elastomeric polymer (e.g. silicone, latex, polyurethane, etc.) that is cured within a shell with a desired inner morphology. In some embodiments, an outer textured surface 62 may be constructed by a fabric overlay used to form texture while the polymer cures.

In particular embodiments, the interior chamber 64, which may be constructed of polymeric material(s) (e.g., polyurethane, silicone, latex, polyurethanes, silicones, latex, nylons, Pebax, PET, PE and other polyolefines, PVC, etc.), is located inside the bulb chamber 60 and fastened to the inner fluid passage channel 30 through methods such as, but not limited to, adhesives, molding, welding, and etc. and will inflate through an increasing presence of fluid through valve 28 and will enable expansion of bulb chamber 60.

In one or more embodiments, the second interior chamber 66, which may be constructed of polymeric material(s) (e.g., polyurethane, silicone, latex, polyurethanes, silicones, latex, nylons, Pebax, PET, PE and other polyolefines, PVC, etc.), will inflate through an increasing presence of fluid and is present in order to fine tune an exemplary occlusion device 10 (as further discussed below).

Figure 3:
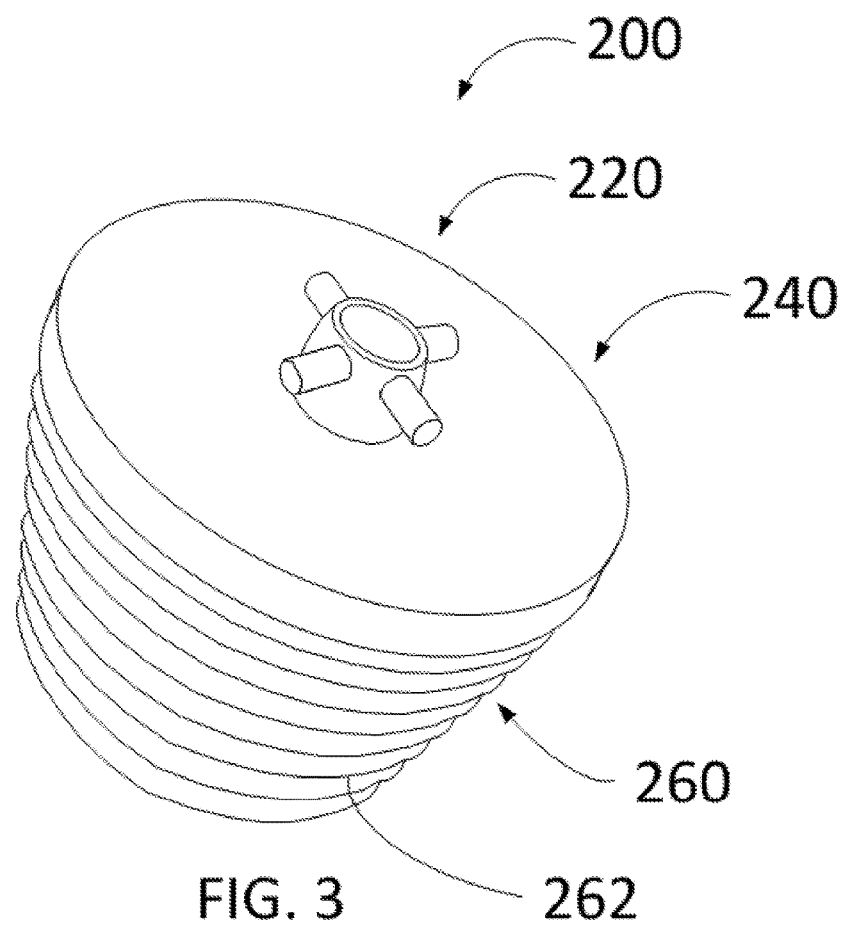
FIG. 3 is a side view of an alternate exemplary occlusion device in a substantially uninflated state according to one embodiment of the present disclosure.
Figure 4:
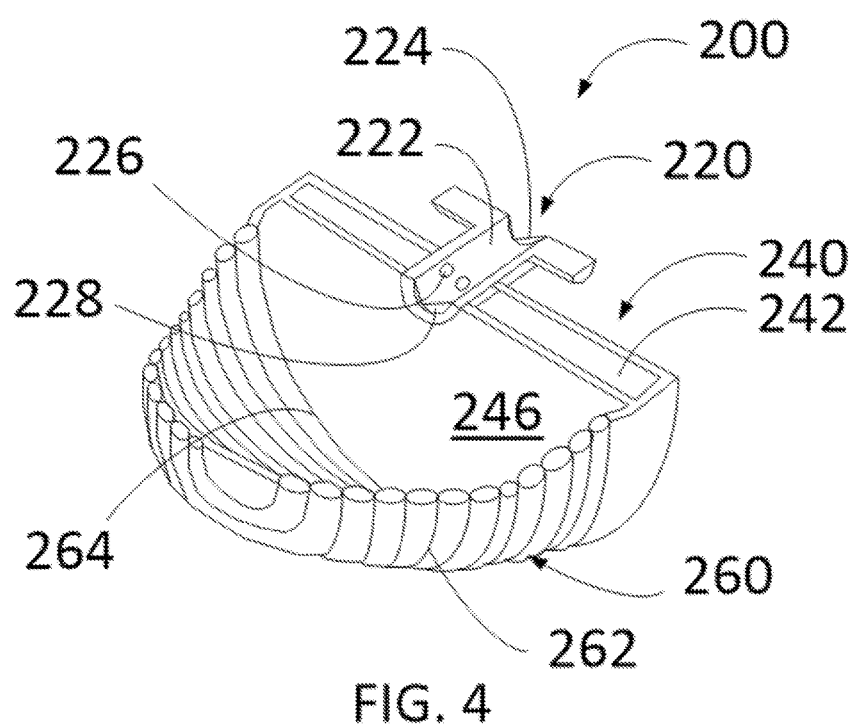
FIG. 4 is a partial cross-sectional view of the alternate exemplary occlusion device in the substantially uninflated state of FIG. 3, according to one embodiment of the present disclosure.

A second exemplary occlusion device 200 is depicted in FIGS. 3 and 4. In the embodiments shown in FIGS. 3 and 4, the exemplary occlusion device 200 includes a secure attachment system 220, fluid passage channel 222, valve 224, fluid passage channel opening 226, valve 228, cap chamber 240, interior cap chamber 242, elastomeric wall 246, bulb chamber 260, textured surface 262, and inner bulb chamber 264.

In one embodiment, the secure attachment system 220, which may be constructed of polymeric material(s) (e.g., polyurethane, silicone, latex, polyurethanes, silicones, latex, nylons, Pebax, PET, PE and other polyolefines, PVC, etc.) or metal material(s) (e.g., aluminum, nitinol, stainless steel, etc.), may be a twist lock that will fasten an exemplary occlusion device 200 to a delivery system through methods such as, but not limited to, adhesives, molding, welding, and etc. and is found at the surface and proximal end of an exemplary occlusion device 200.

In various embodiments, the fluid passage channel 222, which may be constructed of a polymeric material(s) (e.g., polyurethane, silicone, latex, polyurethanes, silicones, latex, nylons, Pebax, PET, PE and other polyolefines, PVC, etc.), is fastened through methods such as, but not limited to, adhesives, molding, welding, and etc. inside the cap chamber 240 and to an elastomeric wall 246, and will allow the transport of fluid to cap chamber 240 and bulb chamber 260.

According to particular embodiments, the valve 224, which may be constructed of polymeric material(s) (e.g., polyurethane, silicone, latex, polyurethanes, silicones, latex, nylons, Pebax, PET, PE and other polyolefines, PVC, etc.), is operatively fastened through methods such as, but not limited to, adhesives, molding, welding, and etc. to the secure attachment system 220 and will control the transport of fluid into and out of the fluid passage channel 222. In various embodiments, the valve 224 is a one-way valve. In one or more embodiments, the valve 224 is a check valve. In some embodiments, the valve 224 is any other suitable type of valve, such as, for example, duckbill valve, umbrella valve, and Belleville valve.

In various embodiments, the fluid passage channel opening 226 is generally circular in shape and is configured to allow the transport of fluid from the fluid passage channel 222 to the cap chamber 240. In some embodiments, the fluid passage channel opening 226 may be an elliptical, ovular, etc. shape. In one or more embodiments, the fluid passage channel opening 226 contains a one-way valve, which may be constructed of polymeric material(s) (e.g., polyurethane, silicone, latex, polyurethanes, silicones, latex, nylons, Pebax, PET, PE and other polyolefines, PVC, etc.). In at least one embodiment, this valve may be a check valve. In some embodiments, the valve may be any other suitable type of valve, such as, for example, duckbill valve, umbrella valve, and Belleville valve.

In some embodiments, the valve 228, which may be constructed of polymeric material(s) (e.g., polyurethane, silicone, latex, polyurethanes, silicones, latex, nylons, Pebax, PET, PE and other polyolefines, PVC, etc.), is operatively fastened through methods such as, but not limited to, adhesives, molding, welding, and etc. to the elastomeric wall 246 and is configured to control the transport of fluid from the fluid passage channel 222 to the bulb chamber 260.

In various embodiments, the valve 228 is a one-way valve. In one or more embodiments, the valve 228 is a check valve. In some embodiments, the valve 228 is any other suitable type of valve, such as, for example, duckbill valve, umbrella valve, and Belleville valve.

In at least one embodiment, the cap chamber 240, which may be constructed of polymeric material(s) (e.g., polyurethane, silicone, latex, polyurethanes, silicones, latex, nylons, Pebax, PET, PE and other polyolefines, PVC, etc.), is found at a proximal end of the exemplary device 200, the elastomeric wall 246, and the bulb chamber 260 and will expand in size as an interior cap chamber 242 is inflated with fluid.

In one embodiment, the interior cap chamber 242, found inside cap chamber 240, is configured to laterally expand due to an increasing presence of fluid transported through a fluid passage channel 222 and fluid passage channel opening 226.

In particular embodiments, the elastomeric wall 246, which may be constructed of polymeric material(s) (e.g., polyurethane, silicone, latex, polyurethanes, silicones, latex, nylons, Pebax, PET, PE and other polyolefines, PVC, etc.), is located between the cap chamber 240 and the inner bulb chamber 264. The elastomeric wall 246 is configured to expand as fluid is transported in inner cap chamber 242 and inner bulb chamber 264.

In one embodiment, the bulb chamber 260, which may be constructed of polymeric material(s) (e.g., polyurethane, silicone, latex, polyurethanes, silicones, latex, nylons, Pebax, PET, PE and other polyolefines, PVC, etc.), is located at the distal end of the exemplary device 200 and includes surface texture 262 and the inner bulb chamber 264. In particular embodiments, the bulb chamber 260 will expand in size as the inner bulb chamber 264 is inflated with fluid.

In various embodiments, surface texture 262 is a ribbed pattern found on bulb chamber 260 and is configured to provide attachment of the exemplary device 200 to a left atrial appendage. In some embodiments, the surface texture 262 cis an angled pattern, checkered pattern, etc.

In one embodiment, the inner chamber 264, found inside bulb chamber 260 and at a distal end of the exemplary device 200, the cap chamber 240, and the elastomeric wall 246, is configured to be inflated through an increasing presence of fluid through a fluid passage channel 222.

Figure 5:
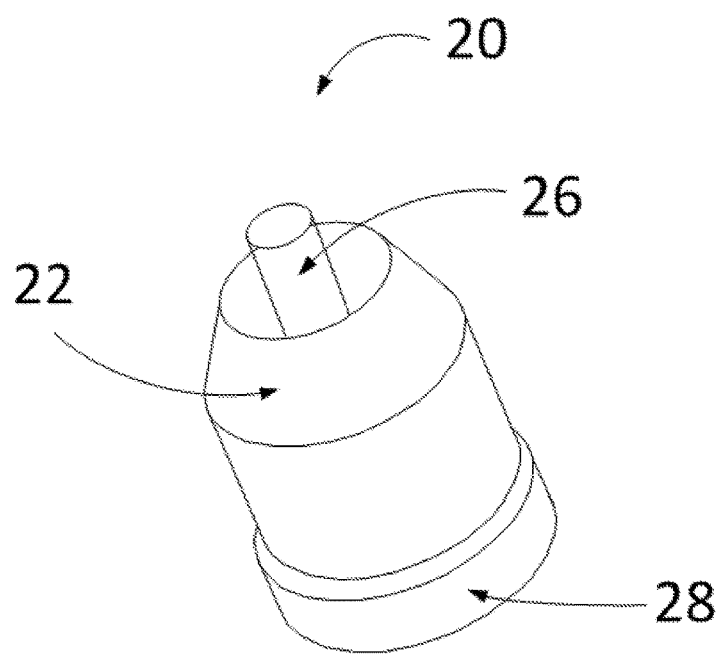
FIG. 5 is a perspective view of a portion of an exemplary connection system of the exemplary occlusion device of FIG. 1, according to one embodiment of the present disclosure.
Figure 6:
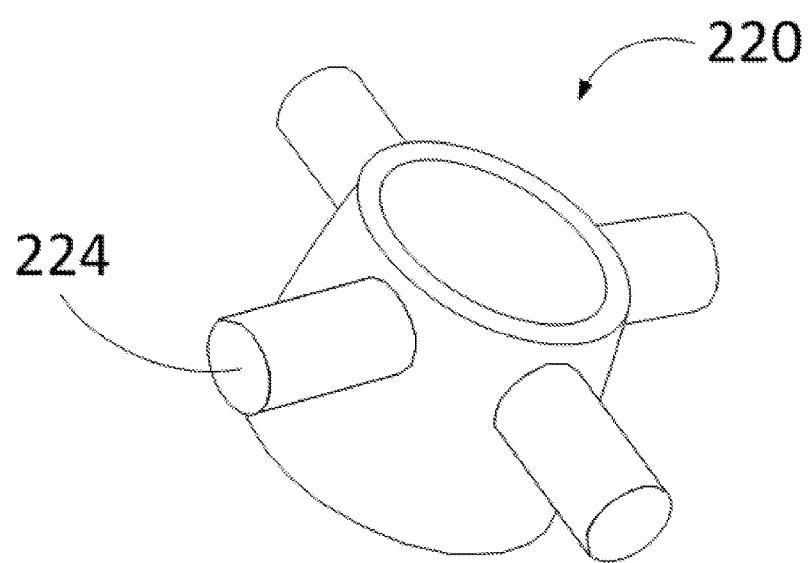
FIG. 6 is a perspective view of a portion of an exemplary connection system of the exemplary occlusion device of FIG. 2, according to one embodiment of the present disclosure.

FIGS. 5 and 6 depict portions of exemplary connection systems 20 and 220. In the embodiment shown in FIG. 5, connection system 20 includes an attachment method 22, a fluid delivery method 26, and an operative fastener 28.

In one embodiment, the attachment method 22, which can be made of metal material(s), is found at a proximal end of an exemplary connection 20 and can be a helical thread configured to allow secure attachment of an exemplary left atrial appendage device to a device delivery system.

In one embodiment, the fluid delivery method 26, which may be made of polymeric material(s) (e.g., polyurethane, silicone, latex, polyurethanes, silicones, latex, nylons, Pebax, PET, PE and other polyolefines, PVC, etc.) or metal material(s) (e.g. nitinol, stainless steel, aluminum, etc.), is located inside exemplary connection 20 and will allow attachment of a fluid delivery method from a delivery system.

In one embodiment, the operative fastener 28, which may be constructed of metal material(s) or polymeric material(s) (e.g., polyurethane, silicone, latex, polyurethanes, silicones, latex, nylons, Pebax, PET, PE and other polyolefines, PVC, etc.), is located at a distal end of the exemplary connection 20 and is configured to be fastened to an exemplary occlusion device 10 through methods such as, but not limited to, adhesives, welding, and etc.

In the embodiment shown in FIG. 5, the connection system 220 includes an attachment method 224. In one embodiment, the attachment method 224 is a twist lock, which may be constructed of polymeric material(s) (e.g., polyurethane, silicone, latex, polyurethanes, silicones, latex, nylons, Pebax, PET, PE and other polyolefines, PVC, etc.) or metal material(s) (e.g., aluminum, nitinol, stainless steel, etc.), and is configured to allow secure attachment of the exemplary occlusion device 200 to a device delivery system.

Figure 7:
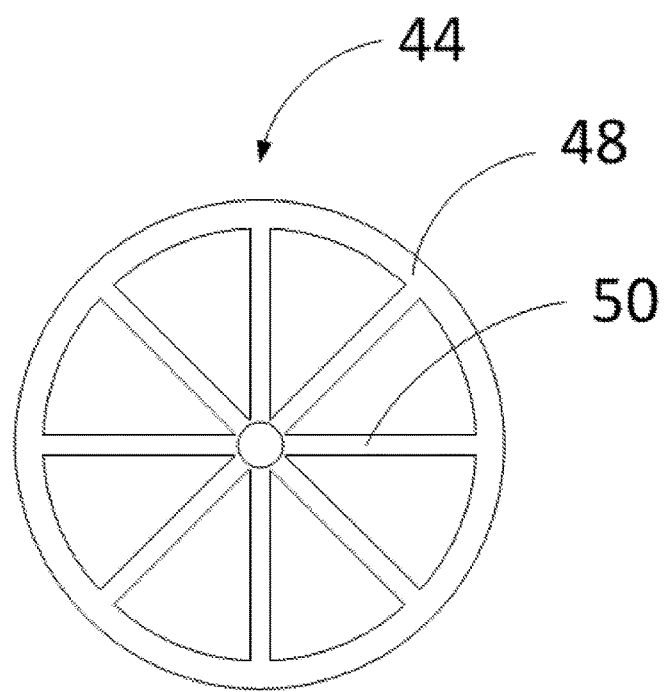
FIG. 7 is a top view of an exemplary fluid ring of the exemplary occlusion device of FIG. 1, according to the one embodiment of the present disclosure.

FIG. 7 shows an exemplary fluid ring 44. In the embodiment shown, the fluid ring 44 includes an outer fluid ring channel 48 and an inner ring transport channel 50.

In one or more embodiments, the outer fluid ring channel 48, which may be constructed of polymeric material(s) (e.g., polyurethane, silicone, latex, polyurethanes, silicones, latex, nylons, Pebax, PET, PE and other polyolefines, PVC, etc.), may be circular shaped, ovular shaped, elliptical shaped, etc. and inflated through a transport of fluid through the inner ring transport channel 50.

In various embodiments, the inner transport channel 50, which may be constructed of polymeric material(s) (e.g., polyurethane, silicone, latex, polyurethanes, silicones, latex, nylons, Pebax, PET, PE and other polyolefines, PVC, etc.), is a substantially straight channel configured to deliver fluid to the outer fluid ring channel 48 for the purposes of inflating the exemplary fluid ring 44.

It will be understood by one of ordinary skill in the art that the fluid ring 44 is one exemplary embodiment of a mechanism for inflating the cap 42. In particular embodiments, other mechanisms may be incorporated into an occlusion device, such as, for example an inner cap chamber that can laterally expand by an increase presence of fluid in order to provide occlusion at a first portion of a left atrial appendage.

Figure 8:
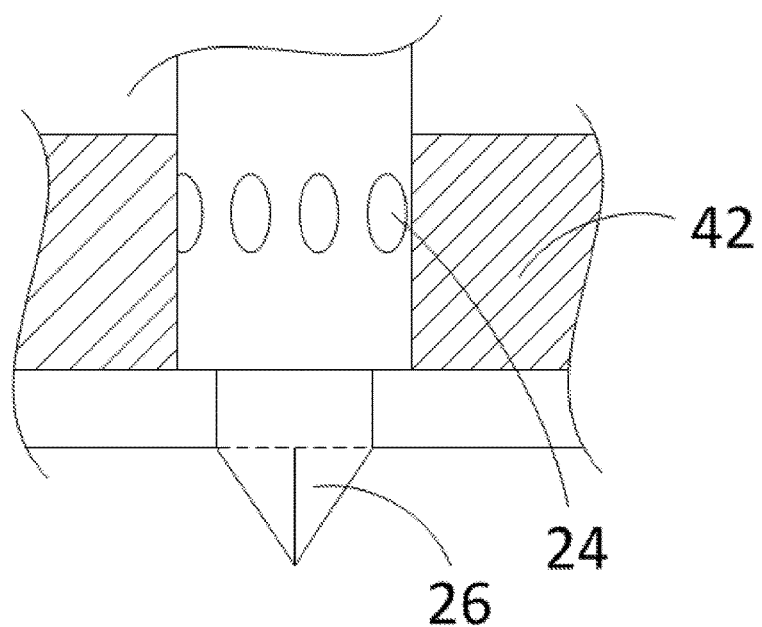
FIG. 8 is a partial cross-sectional view of the exemplary occlusion device of FIG. 1, according to one embodiment of the present disclosure.

FIG. 8 shows a partial cross-section of the exemplary occlusion device 10. In particular, FIG. 8 shows the one or more fluid passage channels 24, the valve 26, and the cap body 42.

In various embodiments, the fluid passage channel 24 contains one or more channels, which may be constructed of polymeric material(s) (e.g., polyurethane, silicone, latex, polyurethanes, silicones, latex, nylons, Pebax, PET, PE and other polyolefines, PVC, etc.), configured to deliver fluid through an opening (which may be a circular, elliptical, or ovular shape, and defined by fluid passage body 22) to an exemplary fluid ring 44.

In some embodiments, the valve 26, which may be constructed of polymeric material(s) (e.g., polyurethane, silicone, latex, polyurethanes, silicones, latex, nylons, Pebax, PET, PE and other polyolefines, PVC, etc.), is located at the proximal end of the fluid passage body 22 and is configured to allow fluid insertion into the bulb chamber 60. In various embodiments, the valve 26 is a one-way valve. In one or more embodiments, the valve 26 is a check valve. In some embodiments, the valve 26 is any other suitable type of valve, such as, for example, duckbill valve, umbrella valve, and Belleville valve.

In one embodiment, the cap body 42, which may be constructed of polymeric material(s) (e.g., polyurethane, silicone, latex, polyurethanes, silicones, latex, nylons, Pebax, PET, PE and other polyolefines, PVC, etc.), surrounds fluid passage body 22 and exemplary fluid ring 44 and provides structure and support for cap body 40 and an exemplary fluid ring 44. In some embodiments, the cap body 42 is constructed through thermal welding or molding techniques. In other embodiments, the cap body 42 can be an integral structure of the cap chamber.

As will be understood from the present disclosure, the exemplary devices described herein may be used in any suitable way. In particular embodiments, the exemplary devices described herein may be used for occlusion of a left atrial appendage. In various embodiments, the exemplary devices described herein may be used for the occlusion of a left ventricle, atrial septal wall, patent foramen ovale, etc.

Exemplary Device Use Case

FIGS. 9-12 depict an exemplary device use case. In particular, FIGS. 9-12 depict an exemplary device as used within a left atrial appendage (LAA) within a patient's heart. Exemplary devices described herein may be used in to occlude the LAA to, for example, help prevent a stroke in the patient. Due to a high prevalence of thrombus forming in the LAA of atrial fibrillation (AF) patients, occluding the LAA may prevent a majority of thrombus formation and thus reduces the risk of ischemic stroke.

A left atrial appendage closure (LAAC) procedure for a particular patient is briefly described. This exemplary procedure is included to further promote an understanding of the exemplary devices and processes disclosed herein and is not necessarily intended to be limiting. The exemplary LAAC procedure for the particular patient may be done under local or general anesthesia in a catheterization lab using standard transseptal techniques. The exemplary procedure may last about one hour and the patient will stay overnight at a hospital post implantation in order to monitor any adverse effects.

Continuing with this exemplary procedure, a transesophageal echocardiogram (TEE) is performed to measure the LAA to determine occlusion size. In this exemplary procedure, after directing the access sheath from the right femoral vein, a transseptal puncture will occur to allow for the access sheath to be placed into the left atrium. An access sheath, in this exemplary procedure, will then be carefully placed into the proximal portion of the LAA over a catheter. Continuing with this exemplary procedure, an occlusion device is prepped by connecting to the delivery system, inserted into the access sheath, and finally, directed to the target left atrial appendage under conventional imaging techniques, including TEE and fluoroscopic guidance (fluoro). In this exemplary procedure, the occlusion device is then deployed into the LAA, and positioning and occlusion is confirmed via imaging.

Figure 9:
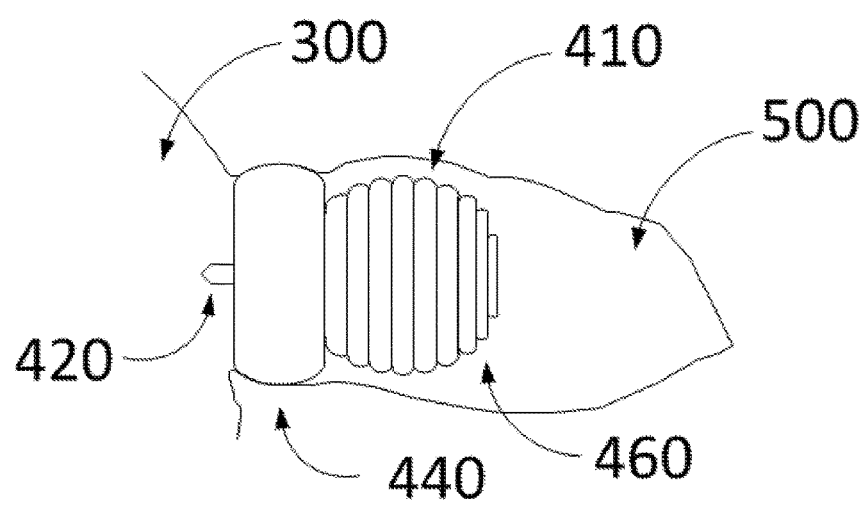
FIG. 9 is side view of an exemplary occlusion device in a partially inflated state in an exemplary left arterial atrium environment, according to one embodiment of the present disclosure.

Turning now to FIG. 9, this figure depicts a patient's heart 300 and a partially inflated exemplary occlusion device 410 within the patient's LAA 500. As will be understood from the discussion herein, the occlusion device 410, in one or more embodiments, is attached to the catheter delivery system and travels through the access sheath. In particular embodiments, upon confirmation of position at the LAA from TEE and fluoro, the device 410 is inflated by inserting fluid using an injection apparatus. According to various embodiments, the fluid used in the present method should be of low viscosity to allow for ease of transportation through the delivery system but create enough pressure inside the occlusion device to allow for expansion and rigidity (e.g., saline, sterile water, contrast, polymerizing agents, and various hydrogels). In various embodiments, partial inflation occurs when cap chamber 440 has been inflated while bulb chamber 460 remains uninflated. In some embodiments, partial inflation occurs when bulb chamber 460 is inflated while cap chamber 440 remains uninflated.

In at least one embodiment, the connection system 420 includes the point of attachment and contact between the delivery system and the occlusion device 410 along with the area to facilitate fluid insertion. In one embodiment, an injection apparatus is inserted inside the connection system 420 to inflate the occlusion device 410. In the embodiment shown in FIG. 9, the cap chamber 440 has been inflated to fit the LAA 500 opening anatomy and acts as a barrier to blood flow from the left atrium (LA) 300. In this embodiment, the uninflated bulb chamber 460 is void of inner material or fluid.

Figure 10:
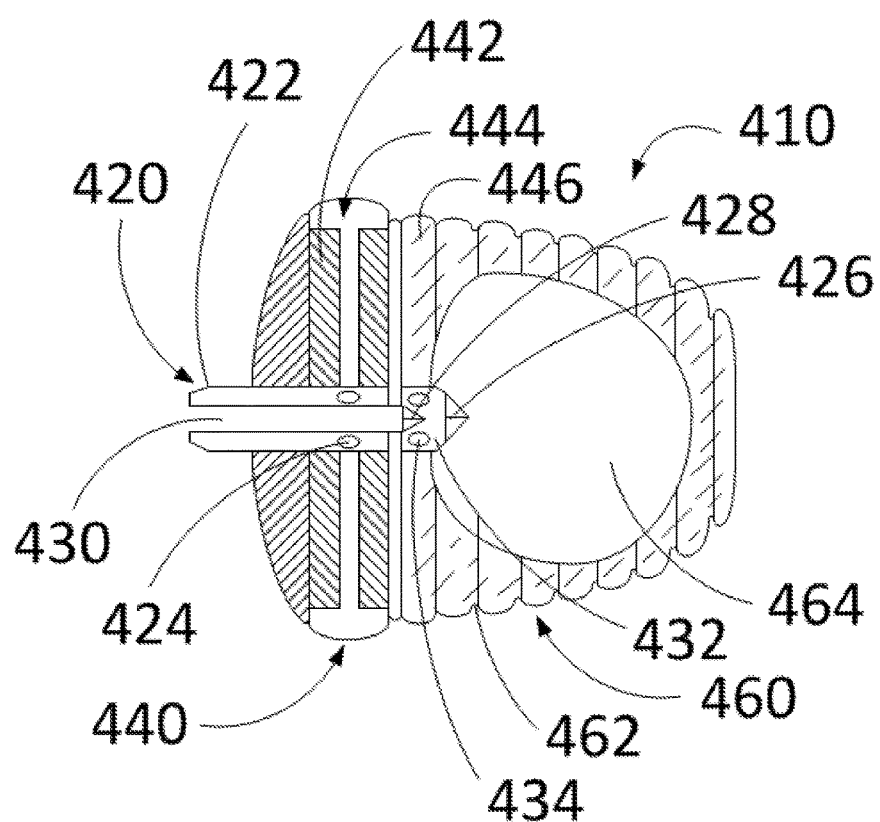
FIG. 10 is a partial cross-sectional view of the partially inflated exemplary occlusion device of FIG. 9, according to one embodiment of the present disclosure.

FIG. 10 depicts a partial cross-sectional view of the exemplary partially inflated device 400 as shown in FIG. 9. In various embodiments, the connection system 420 contains an attachment method 422, which is configured to attach the device 410 to the delivery system and to support transportation and positioning of the device 410 to the LAA. In particular embodiments, a fluid passage body 430 is opened by an injection apparatus and provides a pathway for the apparatus to travel to the cap chamber 440 or bulb chamber 460. In at least one embodiment, fluid passage channels 424 of the cap chamber 440 are configured to enable fluid to travel from the connection system 420 to the outer cap fluid ring 444 to provide outward expansion of the cap chamber 440. According to particular embodiments, a fluid ring 444 is surrounded by a cap body 442 to provide rigidity and reduced expansion towards the LA. In some embodiments, valves 426, 428, operatively fastened through methods such as, but not limited to, adhesives, molding, welding, and etc. At the proximal and distal end of an inner fluid passage channel 432, respectively, are configured to control backflow of fluid and to separate the second internal chamber 466 from the internal bulb chamber 464. In one or more embodiments, an inner fluid passage channel opening 434 allows fluid to calculatedly expand the bulb chamber 460 to allow an exemplary device 410 to adapt to a surrounding left atrial appendage anatomy and provide full occlusion. According to at least one embodiment, the bulb chamber 460 includes a bulb exterior 462, which may include combinations of texturing, ridges, coatings, and surface modification to improve compliance, adhesion to the LAA, and tissue growth. In particular embodiments, as the injection apparatus continues to inflate the device, the bulb chamber 460 increases with fluid, causing a pressure to outwardly expand until an exemplary device 410 adapts to a surrounding left atrial appendage anatomy and provides full occlusion of the LAA body.

Figure 11:
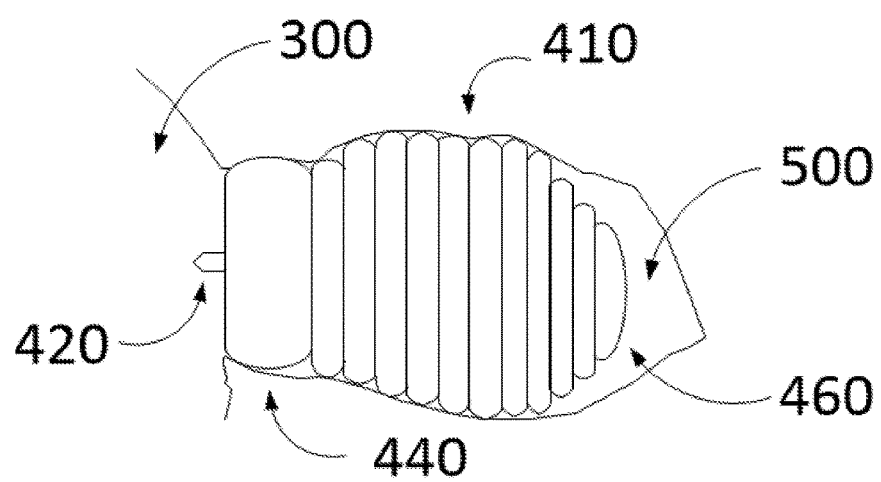
FIG. 11 is side view of an exemplary occlusion device in an inflated state in an exemplary left arterial atrium environment, according to one embodiment of the present disclosure.

Turning now to FIG. 11, this figure depicts a patient's heart 300 and a more fully inflated exemplary occlusion device 410 within the patient's LAA 500. As will be understood from the discussion herein, the occlusion device 410 is inflated fully to adapt to the LAA anatomy 500 and occlude the LAA 500 such that LAA 500 is blocked from the blood flow of the LA 300. According to one or more embodiments, upon confirmation that fully inflated device 410 is inflated to fully adapt to the LAA 500, the connection system 420 is configured to enable removal of the injection apparatus from the device 410, which remains in the LAA 500. In at least one embodiment, the connection system 420 is also the area of disconnect between the delivery system and the device 410. In some embodiments, the delivery system and the access sheath then travel out of the heart 300 and exit the right femoral vein. In various embodiments, the cap chamber 440 assumes the anatomy of the orifice of the LAA 500, and the bulb chamber 460 assumes the anatomy of the body of the LAA 500.

Figure 12:
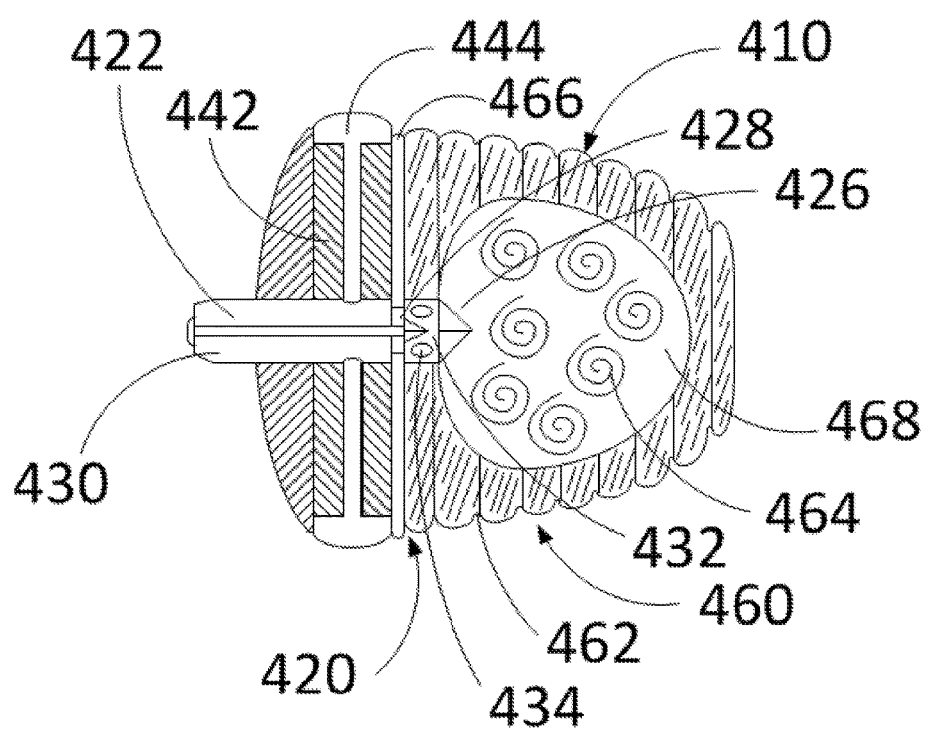
FIG. 12 is a partial cross-sectional view of the inflated exemplary occlusion device of FIG. 11, according to one embodiment of the present disclosure.

FIG. 12 depicts a partial cross-sectional view of the partially inflated device 410 as shown in FIG. 11. In particular embodiments, upon confirmation of the device being fully inflated (as discussed above), the connection system 420 begins to close as the injection apparatus is removed from the fluid transport channel 430. In one or more embodiments, the attachment method 422 is configured for detachment between the device 410 and the delivery system. In at least one embodiment, the fluid passage channels 424 are filled with a fluid to maintain expansion and rigidity of the cap chamber 440. In many embodiments, the cap body 442 maintains the structure and rigidity of the cap chamber 440. In particular embodiments, the outer cap fluid ring 444 is filled with fluid and maintains the interaction between the edges of the device 410 and the LAA orifice. According to at least one embodiment, the valves 426, 428 close once the injection apparatus is removed and prevent fluid movement among chambers 440, 460, 466. In particular embodiments, with a fully inflated bulb chamber 460, the inner bulb chamber 464 is filled with a fluid 468 to maintain shape and allows the bulb exterior 462 to interact with the LAA.

Alternate Embodiments

Alternate Structures

In a first alternate embodiment, an exemplary device may include a balloon that expands through mechanical supports. In this first alternate embodiment, a nitinol or shape memory structure can be inserted inside a balloon, and after the device exits the delivery system, the structure expands to a particular morphology.

Various embodiments of the device herein are depicted as an acorn-shaped body, but the device may be in suitable alternate shapes, including cylindrical, bell-shaped, and ovular.

In some embodiments, an exemplary device may include features to further reduce dislodgement of the device from an LAA. In these embodiments, retention members may be attached to the balloon and may be hooks or coils made of nitinol, alloys, various grades of steel, or different shape-memory materials.

In particular embodiment, the bulb chamber exterior of the device (as discussed herein) may include various coatings or fabrics to promote healing, tissue growth, antithrombogenicity, microbial stability, and adhesion. In this particular embodiment, suitable fabrics may include, but are not limited to ePTFE, PET, and Dacron. Continuing with this particular embodiment, appropriate coatings may include or be from fibronectin, gelatin, fibrinogen, collagen IV, VEGF, polyurethane, fluorosilicone, Bactroban®, Cloramex®, Flamazine®, Fucidin®, Naseptin®, Terramycin®, hyaluronic acid, fibroblast growth factor, and heparin. An adhesive, sealant, glue, or hydrogel could also be added to the device exterior to promote adhesion.

Various embodiments, of the internal portion of the device may include alternate constructions. In some embodiments, the device may be constructed with one or more chambers. In one embodiment, a device design is depicted with two bulb chambers. In some embodiments, one chamber may be made as only one bulb chamber inflation state is needed to fully inflate the balloon. In at least one embodiment, if multiple, separate chambers are constructed, multiple valves and inflation states may be used to control full inflation. In addition, in particular embodiments, the balloon may not feature multiple inner chambers or may exhibit multiple inner chambers. In these particular embodiments, no secondary inner chambers may reduce the number of valves as well as internal structures to separate layers of the balloon. Alternatively, in embodiments with more than one inner chamber, various layers of the balloon may be constructed of alternating elastomeric materials or allow for multiple inflation methods within one device chamber. In one or more embodiments, multiple lumens may require increased number of valves. In addition, more than one connection system can be built to connect a delivery system to multiple chambers separately.

In particular embodiments, the cap body and thicknesses of the balloon may modify shape and internal features of the balloon. In some embodiments, the cap body may be removed or vary in morphology other than in the embodiments shown in the figures and described above. In one embodiment, passage channels may not be constructed, and the inner cap chamber may be constructed as a void. According to particular embodiments, varying thickness of the cap may alter the shape of the cap chamber and varying thicknesses of the bulb chamber may also be created to alter inflation morphology or direct fluid transport.

Some embodiments may include varied valve placement. In these embodiments (and others), one or more valves may be located at the proximal end of the connection system and may be configured to interface with the exterior of the device and the cap chamber. According to particular embodiments, the exemplary device may include one or more valves located within the passage channels. In some embodiments, the exemplary device may include additional valves defined by the openings of lumens. In at least one embodiment, multiple chambers may be connected with no valves to provide a more open connection system for fluid to travel between chambers. Such valves may include check valves, duckbill valves, and relief valves.

Alternate Use Cases

In particular embodiments, the balloon may be configured to be inflated at various states, whether the cap chamber is inflated in the first or last state. In some embodiments, the distal portion of the injection apparatus may be located in the cap chamber as an initial step, allowing for the cap chamber to be inflated first. Continuing with this embodiment, the apparatus can then be pushed toward the bulb portion, allowing for a consecutive inflation state. The injection apparatus, in this embodiment, can then be removed. In alternate embodiments, the injection apparatus can be placed in the bulb chamber initially, and the apparatus is removed after the cap chamber is fully inflated.

As will be understood by one of ordinary skill in the art, the device and delivery system may also be delivered to the LAA from a different mechanism than from the right femoral vein. In various embodiments, a catheter can also be used from the axillary, brachial, or radial arteries as well as the lumbar aorta to deliver the device to the LAA. In these embodiments, the operator must be familiar with these alternative percutaneous routes, and these alternatives may limit sizing of the delivery system.

The device can be used for general soft tissue closure due to customizability, in some embodiments. In particular embodiments, customizability is provided by allowing control of inflation and sizing of the device, and the material properties allow for conformability with surrounding structures. In various embodiments, softer material used in the construction of the device may reduce risks such as tearing and perforation of the LAA or other tissue or organs. In some embodiments, these characteristics may be appropriate for closure of atrial septal defects (ASDs) and patent foramen ovales (PFOs), which are defects found in the atrial septal wall. As further discussed above, although the device is depicted with an acorn-shaped body, in particular embodiments, the device can assume a more dumbbell shape to occlude ASDs and PFOs.

CONCLUSION

Accordingly, the reader will see that devices described herein may be used to close off an appendage or any soft tissue defect or hole, be customizable by conforming to the size and shape of the appendage, defect, or hole, easily retrievable by removing one or more fluids, reduce tearing and perforation due to the soft polymeric material, and securely attach to the appendage, defect, or hole due to its unique textured pattern.

The foregoing description of the exemplary embodiments has been presented only for the purposes of illustration and description and is not intended to be exhaustive or to limit the embodiments discussed herein to the precise forms disclosed. Many modifications and variations are possible in light of the above teaching.

The embodiments were chosen and described in order to explain the principles of the present disclosure and their practical application so as to enable others skilled in the art to utilize the present disclosure and various embodiments and with various modifications as are suited to the particular use contemplated. Alternative embodiments will become apparent to those skilled in the art to which the present disclosure pertains without departing from their spirit and scope.

We claim:

1. An occlusion device for occluding a left atrial appendage, the device comprising:
   a connection system configured for attaching an occlusion device to a fluid transport device; and
   an inflatable balloon operatively fastened to the connection system, the inflatable balloon comprising a cap chamber and a bulb chamber, the cap chamber and the bulb chamber separated by an elastomeric wall, wherein:
   the connection system a) extends through the cap chamber and at least partially through the bulb chamber, b) is configured for delivering one or more fluids to the cap chamber and the bulb chamber, and c) includes one or more valves;
   the cap chamber is substantially disc-shaped, includes a fluid ring, and is configured to expand outwardly in a lateral direction from a center of the cap chamber to substantially fill a first portion of a left atrial appendage;
   the bulb chamber is configured to expand outwardly to substantially fill a second portion of the left atrial appendage; and
   the connection system comprises:
     a first valve located in the cap chamber for preventing fluid from traveling from the cap chamber to an exterior of the device; and
     a second valve located in the bulb chamber.

2. The device of claim 1, wherein the inflatable balloon comprises a single polymer structure.

3. The device of claim 2, wherein the single polymer structure comprises a non-porous exterior surface for preventing permeation.

4. The device of claim 1, wherein the connection system further comprises a channel for transporting fluid to the cap chamber and the bulb chamber.

5. The device of claim 1, wherein the bulb chamber comprises an exterior for adhesion to the left atrial appendage.

6. The device of claim 5, wherein the exterior of the bulb chamber comprises a coating for promoting tissue growth within the left atrial appendage.

7. The device of claim 5, wherein the exterior of the bulb chamber comprises an irregular texture for adhesion to the left atrial appendage.

8. A left atrial appendage occlusion device, the device comprising:
  a connection system configured for attaching the device to a fluid transport device, the connection system extending at least partially through each of a cap chamber and a bulb chamber of an inflatable balloon and is configured for delivering one or more fluids to the cap chamber and the bulb chamber; and
  the inflatable balloon, wherein the inflatable balloon is operatively connected to the connection system and comprises:
    the cap chamber, wherein the cap chamber is configured to expand outwardly in a lateral direction from a center of the cap chamber and includes a fluid ring; and
    the bulb chamber, wherein the bulb chamber is separated from the cap chamber by an elastomeric wall and is configured to expand outwardly to substantially fill a void, wherein:
    the connection system comprises:
      a channel for transporting fluid to the cap chamber and the bulb chamber;
      a first valve located in the cap chamber for preventing fluid from traveling from the cap chamber to an exterior of the device; and
      a second valve located in the bulb chamber.

9. The device of claim 8, wherein the inflatable balloon comprises a single polymer structure.

10. The device of claim 9, wherein the single polymer structure comprises a non-porous exterior surface for preventing permeation.

11. The device of claim 10, wherein the bulb chamber is configured to expand outwardly to substantially fill a second portion of the left atrial appendage.

12. The device of claim 9, wherein the cap chamber is substantially disc-shaped and is configured to expand outwardly in the lateral direction for substantially filling a first portion of a left atrial appendage of a patient.

13. The device of claim 9, wherein the channel a) defines one or more openings for transporting fluid to the cap chamber, and b) terminates at the second valve.

14. The device of claim 8, wherein the bulb chamber comprises an exterior for adhesion to a biological structure.

15. The device of claim 14, wherein the exterior of the bulb chamber comprises a coating for tissue growth within the biological structure.

16. The device of claim 15, wherein the exterior of the bulb chamber comprises an irregular texture for adhesion to the biological structure.

* * * * *